United States Patent
Malik et al.

(10) Patent No.: US 8,980,550 B2
(45) Date of Patent: Mar. 17, 2015

(54) METHODS FOR MEASURING SAMPLES USING CONSUMER ELECTRONIC DEVICES AND SYSTEMS

(75) Inventors: Imran R. Malik, Pasadena, CA (US); Axel Scherer, Woodstock, VT (US)

(73) Assignee: California Institute of Technology, Pasadena, CA (US)

(*) Notice: Subject to any disclaimer, the term of this patent is extended or adjusted under 35 U.S.C. 154(b) by 430 days.

(21) Appl. No.: 13/009,785

(22) Filed: Jan. 19, 2011

(65) Prior Publication Data

US 2011/0207137 A1  Aug. 25, 2011

Related U.S. Application Data

(60) Provisional application No. 61/297,178, filed on Jan. 21, 2010.

(51) Int. Cl.

| | |
|---|---|
| *C12Q 1/68* | (2006.01) |
| *G01N 31/00* | (2006.01) |
| *G01N 21/64* | (2006.01) |
| *B01L 7/00* | (2006.01) |
| *G01N 21/03* | (2006.01) |
| *G01N 21/84* | (2006.01) |

(52) U.S. Cl.
CPC .............. *G01N 21/6428* (2013.01); *B01L 7/52* (2013.01); *B01L 2300/023* (2013.01); *B01L 2300/0654* (2013.01); *G01N 21/0332* (2013.01); *G01N 21/645* (2013.01); *G01N 2021/6419* (2013.01); *G01N 2021/6421* (2013.01); *G01N 2021/6441* (2013.01); *G01N 2201/0627* (2013.01); *G01N 21/8483* (2013.01)
USPC .......................... 435/6.1; 435/283.1; 422/68.1

(58) Field of Classification Search
None
See application file for complete search history.

(56) References Cited

U.S. PATENT DOCUMENTS

| | | | |
|---|---|---|---|
| 4,930,361 | A | 6/1990 | Nimberger |
| 5,196,830 | A | 3/1993 | Birging |
| 5,272,518 | A | 12/1993 | Vincent |
| 5,508,197 | A | 4/1996 | Hansen |
| 5,820,265 | A | 10/1998 | Kleinerman |
| 5,871,699 | A | 2/1999 | Ruggeri |
| 6,222,619 | B1 | 4/2001 | Herron et al. |
| 6,441,890 | B2 | 8/2002 | Wardlaw et al. |
| 6,544,734 | B1 | 4/2003 | Briscoe et al. |
| 6,902,112 | B2 | 6/2005 | Sadler |
| 7,411,792 | B2 | 8/2008 | Richards et al. |

(Continued)

FOREIGN PATENT DOCUMENTS

| | | |
|---|---|---|
| EP | 1972919 | 9/2008 |
| JP | 2002-139418 | 5/2002 |

(Continued)

OTHER PUBLICATIONS

Restriction Requirement issued for U.S. Appl. No. 12/638,829, filed Dec. 15, 2009 in the name of Imran R. Malik et al.; mailing date: Oct. 20, 2011.

Non-Final Office Action issued for U.S. Appl. No. 12/638,829, filed Dec. 15, 2009 in the name of Imran R. Malik et al.; mailing date: Dec. 16, 2011.

Final Office Action issued for U.S. Appl. No. 12/638,829, filed Dec. 15, 2009 in the name of Imran R. Malik et al.; mailing date: Oct. 23, 2012.

(Continued)

*Primary Examiner* — Betty Forman
(74) *Attorney, Agent, or Firm* — Steinfl & Bruno, LLP

(57) ABSTRACT

Methods for measuring and analyzing biological or chemical samples using consumer electronic devices and systems are described. Moreover, an accessory to enable using devices such as cell phones and smartphones with fluidic illumination chambers are described.

28 Claims, 4 Drawing Sheets

(56) References Cited

U.S. PATENT DOCUMENTS

| | | | |
|---|---|---|---|
| 7,564,541 B2 | 7/2009 | Tuschel | |
| 7,754,153 B2 | 7/2010 | Miyamoto | |
| 8,058,054 B2 | 11/2011 | Owen et al. | |
| 8,071,385 B2 | 12/2011 | Haas et al. | |
| 8,277,760 B2 | 10/2012 | Letho | |
| 8,395,773 B2 | 3/2013 | Malik et al. | |
| 2002/0046614 A1 | 4/2002 | Alley | |
| 2002/0160534 A1 | 10/2002 | Herron et al. | |
| 2003/0109806 A1 | 6/2003 | Weber et al. | |
| 2004/0022677 A1* | 2/2004 | Wohlstadter et al. | 422/52 |
| 2004/0091862 A1 | 5/2004 | Brandenburg et al. | |
| 2004/0152206 A1 | 8/2004 | Davis et al. | |
| 2005/0024636 A1 | 2/2005 | Nakamura | |
| 2005/0036142 A1 | 2/2005 | Oldham et al. | |
| 2005/0042651 A1* | 2/2005 | Vann et al. | 435/6 |
| 2005/0059165 A9 | 3/2005 | Davis et al. | |
| 2005/0099621 A1 | 5/2005 | Vez-Iravani et al. | |
| 2005/0109396 A1 | 5/2005 | Zucchelli et al. | |
| 2005/0282266 A1* | 12/2005 | Teng et al. | 435/286.1 |
| 2006/0186346 A1 | 8/2006 | Wei | |
| 2006/0211071 A1 | 9/2006 | Andre et al. | |
| 2006/0233670 A1 | 10/2006 | Lehto | |
| 2006/0289787 A1 | 12/2006 | Ohbian et al. | |
| 2006/0290934 A1 | 12/2006 | Boekelman | |
| 2007/0084279 A1 | 4/2007 | Huang et al. | |
| 2007/0272039 A1 | 11/2007 | Hermet et al. | |
| 2008/0003649 A1 | 1/2008 | Maltezos et al. | |
| 2008/0176230 A1* | 7/2008 | Owen et al. | 435/6 |
| 2008/0176755 A1* | 7/2008 | Amundson et al. | 506/7 |
| 2009/0050209 A1 | 2/2009 | Rautavuori | |
| 2009/0176661 A1 | 7/2009 | Harding et al. | |
| 2010/0051124 A1 | 3/2010 | Imran | |
| 2010/0120164 A1 | 5/2010 | Salafsky | |
| 2010/0152066 A1 | 6/2010 | Malik et al. | |
| 2010/0184229 A1* | 7/2010 | Haas et al. | 436/50 |
| 2010/0192706 A1 | 8/2010 | Fairs et al. | |
| 2010/0321696 A1 | 12/2010 | Malik et al. | |
| 2011/0104026 A1 | 5/2011 | Yoon et al. | |
| 2011/0151577 A1 | 6/2011 | Zhang et al. | |
| 2011/0207137 A1 | 8/2011 | Malik et al. | |
| 2011/0207313 A1 | 8/2011 | Lim et al. | |
| 2011/0306120 A1 | 12/2011 | Nicholls et al. | |
| 2012/0003631 A1 | 1/2012 | Yu et al. | |
| 2012/0180882 A1 | 7/2012 | Malik et al. | |

FOREIGN PATENT DOCUMENTS

| | | |
|---|---|---|
| JP | 2002-214225 | 7/2002 |
| JP | 2012-100549 | 5/2012 |
| WO | 00/21659 | 4/2000 |
| WO | 2007/102713 | 9/2007 |
| WO | 2011/005487 | 1/2011 |

OTHER PUBLICATIONS

Non-Final Office Action issued for U.S. Appl. No. 12/820,104, filed Jun. 21, 2010 in the name of Imran R. Malik et al.; mailing date: Jun. 6, 2012.
Final Office Action issued for U.S. Appl. No. 12/820,104, filed Jun. 21, 2010 in the name of Imran R. Malik et al.; mailing date: Oct. 10, 2012.
Notice of Allowance issued for U.S. Appl. No. 12/820,104, filed Jun. 21, 2010 in the name of Imran R. Malik et al.; mailing date: Dec. 24, 2012.
PCT International Search Report issued for PCT Application PCT/US2010/039389 filed on Jun. 21, 2010 in the name of California Institute of Technology et al.
PCT Written Opinion issued for PCT Application PCT/US2010/039389 filed on Jun. 21, 2010 in the name of California Institute of Technology et al.
PCT International Search Report mailed on Feb. 7, 2011 for PCT Application PCT/US2010/039389 filed on Jun. 21, 2010 in the name of California Institute of Technology et al.
PCT Written Opinion mailed on Feb. 7, 2011 for PCT Application PCT/US2010/039389 filed on Jun. 21, 2010 in the name of California Institute of Technology et al.
PCT International Search Report mailed on Feb. 3, 2014 for PCT Application PCT/US2013/068170 filed on Nov. 1, 2013 in the name of California Institute of Technology.
PCT Written Opinion mailed on Feb. 17, 2014 for PCT Application PCT/US2010/039389 filed on Jun. 21, 2010 in the name of California Institute of Technology et al.
PCT International Search Report mailed on Feb. 14, 2014 for PCT/US2013/068165 filed on Nov. 1, 2013 in the name of California Institute of Technology.
PCT Written Opinion mailed on Feb. 14, 2014 for PCT/US2013/068165 filed on Nov. 1, 2013 in the name of California Institute of Technology.
PCT International Search Report mailed on Feb. 5, 2014 for PCT/US2013/068172 filed on Nov. 1, 2013 in the name of California Institute of Technology.
PCT Written Opinion mailed on Feb. 5, 2014 for PCT/US2013/068172 filed on Nov. 1, 2013 in the name of California Institute of Technology.
Restriction Requirement mailed on Oct. 20, 2011 for U.S. Appl. No. 12/638,829, filed Dec. 15, 2009 in the name of Imran R. Malik et al.
Final Office Action mailed on Jan. 24, 2014 for U.S. Appl. No. 12/638,829, filed Dec. 15, 2009 in the name of Imran R. Malik et al.
Final Office Action mailed on Oct. 23, 2013 for U.S. Appl. No. 12/638,829, filed Dec. 15, 2009 in the name of Imran R. Malik et al.
Non-Final Office Action mailed on Dec. 16, 2011 for U.S. Appl. No. 12/638,829, filed Dec. 15, 2009 in the name of Imran R. Malik et al.
Non-Final Office Action mailed on Oct. 3, 2013 for U.S. Appl. No. 12/638,829, filed Dec. 15, 2009 in the name of Imran R. Malik et al.
Final Office Action mailed on Oct. 10, 2012 for U.S. Appl. No. 12/820,104, filed Jun. 21, 2010 in the name of Imran R. Malik et al.
Non-Final Office Action mailed on Jun. 6, 2012 for U.S. Appl. No. 12/820,104, filed Jun. 21, 2010 in the name of Imran R. Malik et al.
Notice of Allowance mailed on Dec. 24, 2012 for U.S. Appl. No. 12/820,104, filed Jun. 21, 2010 in the name of Imran R. Malik et al.
Non-Final Office Action mailed on Nov. 26, 2013 for U.S. Appl. No. 13/407,644, filed Feb. 28, 2012 in the name of Imran R. Malik et al.
Restriction Requirement mailed on Sep. 17, 2013 for U.S. Appl. No. 13/407,644, filed Feb. 28, 2012 in the name of Imran R. Malik et al.
PCT Written Opinion mailed on Feb. 3, 2014 for PCT Application PCT/US2013/068170 filed on Nov. 1, 2013 in the name of California Institute of Technology.
PCT International Search Report mailed on Feb. 17, 2014 for PCT Application PCT/US2013/068171 filed on Nov. 1, 2013 in the name of California Institute of Technology.
PCT Written Opinion mailed on Feb. 17, 2014 for PCT Application PCT/US2013/068171 filed on Nov. 1, 2013 in the name of California Institute of Technology.
PCT International Search Report mailed on Feb. 6, 2014 for PCT Application PCT/US2013/068173 filed on Nov. 1, 2013 in the name of California Institute of Technology.
PCT Written Opinion mailed on Feb. 6, 2014 for PCT Application PCT/US2013/068173 filed on Nov. 1, 2013 in the name of California Institute of Technology.
PCT International Search Report mailed on Oct. 16, 2013 for PCT Application PCT/US2013/051461 filed on Jul. 22, 2013 in the name of California Institute of Technology.
PCT Written Opinion mailed on Oct. 16, 2013 for PCT Application PCT/US2013/051461 filed on Jul. 22, 2013 in the name of California Institute of Technology.
PCT International Search Report mailed Feb. 17, 2014 for PCT Application PCT/US2013/068169 filed on Nov. 1, 2013 in the name of California Institute of Technology.
Notice of Allowance mailed on Feb. 28, 2014 for U.S. Appl. No. 13/947,469, filed Jul. 22, 2013 in the name of California Institute of Technology.

* cited by examiner

METHODS FOR MEASURING SAMPLES USING CONSUMER ELECTRONIC DEVICES AND SYSTEMS

CROSS REFERENCE TO RELATED APPLICATIONS

The present application claims priority to U.S. Provisional Application No. 61/297,178, filed on Jan. 21, 2010, and may be related to U.S. patent application Ser. No. 12/638,829 filed on Dec. 15, 2009 and Ser. No. 12/820,104 filed on Jun. 21, 2010, all of which are incorporated herein by reference in their entirety.

FIELD

The present disclosure relates to measuring biological or chemical samples. Moreover, it relates to methods for measuring samples using consumer electronic devices and systems.

BACKGROUND

There is a wide variety of scientific operations in which biological or chemical sampling, measuring and analyzing are performed. Many of these procedures rely on the use of expensive and/or bulky equipment. Low-cost and portable methods can be desirable if accurate results can be obtained.

An example of such operations is PCR (polymerase chain reaction). PCR is a technique used in molecular biology to amplify a portion of DNA (deoxyribonucleic acid) or RNA (after reverse transcription to DNA). In a PCR reaction, the enzyme DNA polymerase generates copies of a target sequence in an exponential fashion. Primers are used to amplify specific sequences and nucleotides are added as material which is assembled by polymerase to make DNA copies.

SUMMARY

According to a first aspect, an accessory configured to connect a consumer electronic device with an illumination chamber, the consumer electronic device comprising a light source and a light detector, the illumination chamber comprising one or more reservoirs, a light coupling structure, and reflective walls to reflect light within the illumination chamber, and a heating element adapted to heat the biological or chemical sample, each of the reservoirs being adapted to contain a biological or chemical sample to produce an emission light is described, the accessory comprising: an excitation filter adapted to filter light from the light source of the consumer electronic device; a light guide adapted to guide the filtered light to the light coupling structure of the illumination chamber; an emission filter adapted to filter the emission light, the emission light adapted to be detected by the light detector of the consumer electronic device; a temperature sensor connected to the heating element of the illumination chamber; a microcontroller; an input/output port, the input/output port adapted to provide power for the accessory and components therein and adapted to provide communication between the consumer electronic device and the accessory; and an electronic switch configured to turn the heating element on and/or off according to instructions from the microcontroller, the microcontroller obtaining temperature information from the temperature sensor, wherein the consumer electronic device is selected from the group consisting of: cell phone, smartphone, digital camera, internet tablet, laptop computer, digital camera, and webcam.

According to a second aspect, a method of connecting a consumer electronic device with an illumination chamber to measure and/or analyze a biological or chemical sample, is described, the method comprising: providing the accessory according to the first aspect; providing an illumination chamber with one or more reservoirs; providing a consumer electronic device, the accessory configured to connect the consumer electronic device with the illumination chamber; aligning the light source of the consumer electronic device to the light coupling structure of the illumination chamber with the light guide on the accessory; aligning the detector of the consumer electronic device to the illumination chamber, the detector configured to detect the emission light from the illumination chamber; and measuring and/or analyzing the emission light detected from the biological or chemical sample.

According to a third aspect, a method of using a cell phone having a vibrator to mix a biological or chemical sample in a reservoir is described, the method comprising: placing the biological or chemical sample in a reservoir; placing an accessory on the cell phone, the accessory adapted to connect the reservoir with the cell phone; placing the reservoir on the accessory; vibrating the cell phone such that the vibration of the cell phone vibrates the accessory and reservoir, the vibration causing the biological or chemical sample to mix.

According to a fourth aspect, an optical system is described, the system comprising: an illumination chamber; the accessory according to a first aspect, the accessory placed on the illumination chamber; and a consumer electronic device, placed on the accessory.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

The embodiments of the present disclosure describe methods to perform medical, biological or chemical procedures through the use of consumer electronic devices. By way of example and not of limitation, a "consumer electronic device" refers to devices such as cell phones, smartphones, digital camera, internet tablets, laptop computer, netbook computers, LEDs, and computer accessories like webcams. Existing components of consumer electronic devices can either be used on their own as an accessory or in addition to existing systems for such biological or chemical applications.

An example involves use of a light on a cell phone or a flash on a digital camera for illumination. Another example can involve use of a battery as a power source from such consumer electronic devices via a USB port. Other examples can include use of devices like a camera, accelerometer, compass, GPS receivers, temperature sensors, and wireless links.

In some cases, software or firmware modifications can be sufficient to conduct such biological or chemical procedures without any hardware modification to the electronic devices. In the case of smartphones, the software application can be easily run from the smartphone. In other cases, an existing system can be modified to be conjoined with the consumer electronic device (e.g., cell phone) to form a new system. Such modifications made for added functionality to the existing can be provided by the original equipment manufacturer (OEM) of the consumer device or can be accomplished by an end-user (e.g., laboratory technician, scientist).

An example of some of the biological or chemical procedures which can be accomplished with the addition of such consumer electronic devices can include: PCR (polymerase chain reaction), qPCR (real-time PCR), water testing based on absorbance and related techniques, food testing, emission and absorption measurements, and electrical impedance and voltammetry based tests.

Figure 1:
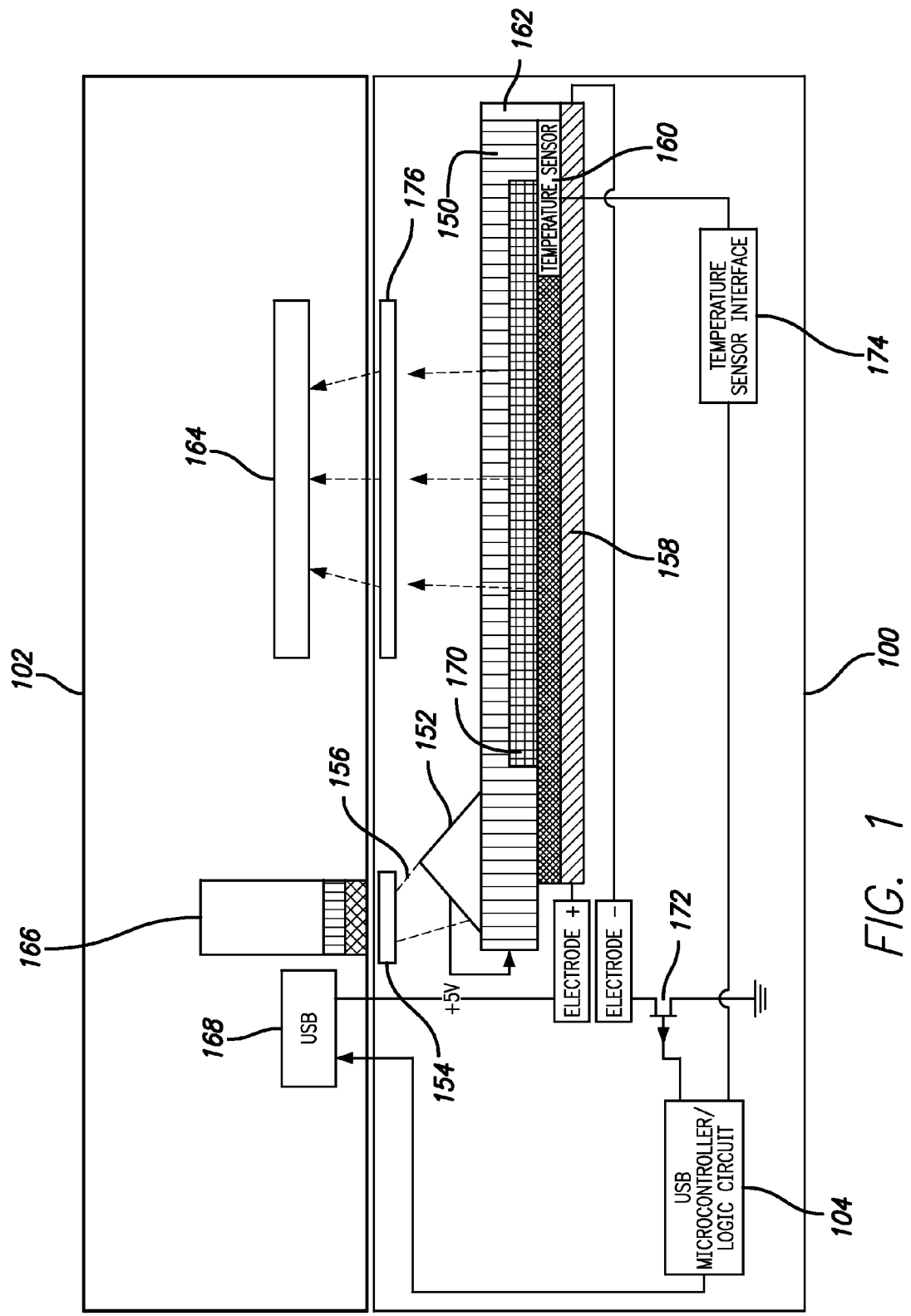
FIG. 1 shows a cross-sectional view of an exemplary illumination chamber connected with a consumer electronic device by way of an accessory between the two.

In an embodiment of the present disclosure as shown in FIG. 1, a consumer electronic device (102) with an onboard light sensor (164) can be used together with a measuring or analysis system, such as a qPCR system (102), whereby the consumer electronic device (102) is connected with the qPCR system (102) through the use of an accessory (100), which will be described throughout the present disclosure. The term 'accessory' is defined as a device that can be added to a device to make the device more useful. Consumer electronic devices (102) can be, for example, cell phones, digital cameras and webcams. Some of these devices comprises a light source (e.g., flash, LED), which can also be used with the accessory. Since many consumer electronic devices (102) have substantially flat surfaces, attaching the accessory (100) with the consumer electronic device (102) can be accomplished with ease.

An exemplary qPCR system can comprise an illumination chamber (150), a reservoir (170), a light coupling structure (152), an excitation filter (154), an emission filter (176), a heater (158), a temperature sensor (160), reflective walls (162), a light source (166), and a detector (167). A similar optical measuring system (e.g., qPCR system) can be found for example in U.S. patent application Ser. No. 12/820,104 incorporated herein by reference in its entirety. Differently from the optical measuring system in U.S. patent application Ser. No. 12/820,104, the qPCR system in FIG. 1 is shown with the detector (164) and the light source (166) as part of the consumer electronic device (102).

A consumer electronic device (102) such as a cell phone is typically made by many different manufacturers where every cell phone can comprise different features, sizes, and shapes. For example, one type of cell phone can have a camera and a flash aligned vertically, whereas in another cell phone, the camera and the flash are aligned horizontally on the back of the cell phone. In other cases, the camera and the flash may be closer or farther apart from one another. Therefore, the accessory (100) can be configured for the different types of consumer electronic devices (102) such that when the light detector (164) (camera) of the cell phone is aligned over the reservoir (170), the light source (166) (flash) is aligned to be able to provide light to the light coupling structure (152) of the qPCR system.

Figure 4:
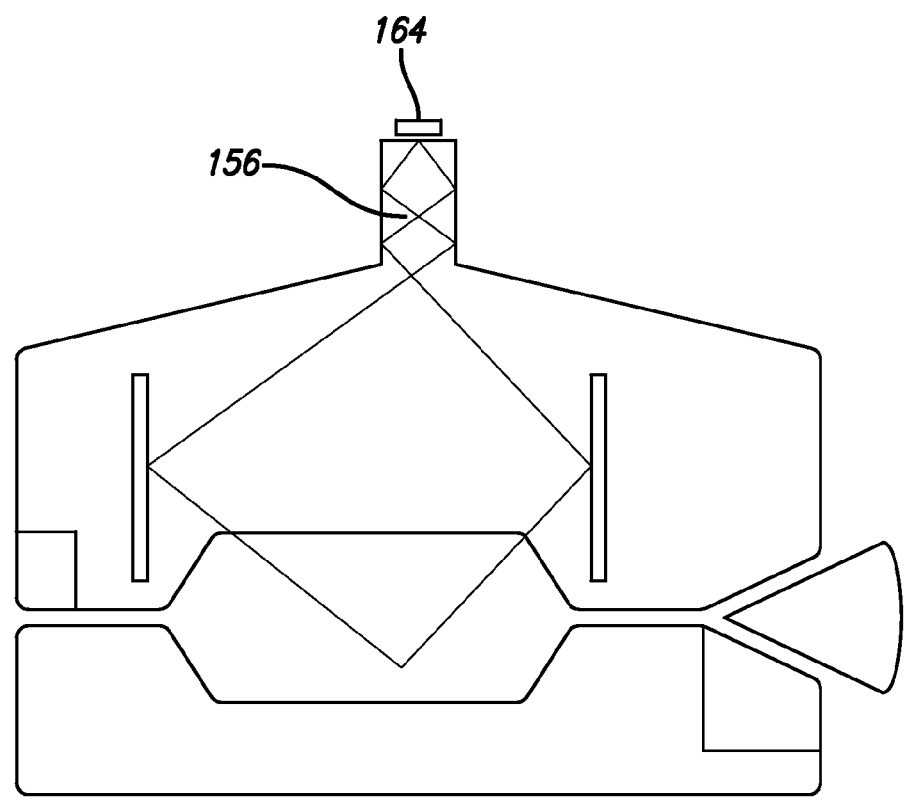
FIGS. 4-6 show top views of alternatives types of the illumination chambers.

The accessory (100) can comprise a light guide (156) to guide the light from the light source (166) through the excitation filter (154) and into the light coupling structure (152) of the illumination chamber (150). Therefore, even though the camera and the flash are not spaced apart precisely equal to the spacing between reservoir (170) and the light coupling structure (152), respectively, the light guide of the accessory (100) can guide the light to a desired location. Furthermore, the light guide (156) shown from a top view in FIG. 4 with the light source (166), can also act as a homogenizer to distribute the intensity of the light uniformly as the light reaches the illumination chamber (150).

When the light source (166) is aligned over the light guide (156), the light can pass through the excitation filter (154) to filter out undesired wavelengths of the light and allow desired wavelength of the light to pass through the light guide (156) and into the light coupling structure (152). The light coupling structure (152) can couple the excitation light into the illumination chamber (150) to illuminate a sample volume within the reservoir (170), such that the excitation light can reflect within the illumination chamber (150) and remain confined within the illumination chamber (150) by way of total internal reflection.

As an example, when the biological or chemical sample is coated with fluorophore, and exposed with excitation light, the fluorophore will emit emission light. Such emission light can be detected by the light detector (164) when imaged through an emission filter (176) to measure emission. In the case where the consumer electronic device (102) is a smartphone, the smartphone can be programmed with a software application to analyze the measured emission to perform, for example, a viral load determination or a melting curve analysis. Results obtained from such analyses can be displayed on the screen of the consumer electronic device (102) (e.g., smartphone screen) and, if desired, such results can be either stored on the smartphone memory or transferred to other devices such as a desktop computer or emailed to another user (e.g., doctor, scientist).

In an exemplary qPCR cycle, the temperature of the qPCR system is raised and lowered multiple times in a controlled manner. In an embodiment of the present disclosure, a microcontroller (104) within the accessory (100) can be programmed with a software application to control the temperature by obtaining temperature measurements of the illumination chamber (150) with a temperature sensor (160) and turning on the heater (158) when it is desired to raise the temperature and turning off the heater (158) when it is desired to lower the temperature.

The heater (158) can be configured to receive power from its own power source within the accessory (100) or from the consumer electronic device (102). In the case where the consumer electronic device (102) provides power to the heater (158), the connection between the consumer electronic device (102) and the accessory (100) can be made by way of, for example, a USB port (168) connection.

In yet another embodiment, the USB port (168) connection can also provide power not only to the heater (158) but also to the microcontroller (104) and other associated electronic components such as an electronic switch (172). For example, in FIG. 1, the microcontroller (104) as well as the electronic switch (172) and the heater (158) each receive power through the USB port (168) from the consumer electronic device (102). The microcontroller (104) is connected to a temperature sensor interface (174) and a temperature sensor (160). Thus, when the temperature sensor (160) senses that the temperature of the illumination chamber (150) is low, the microcontroller (104) can determine that the heater (158) should be turned on or off based on voltage applied to an electronic switch (172). Such electronic switch (172) can be turned on and off by a pulse-width modulated voltage available from the USB port (168) or another external power source.

Additionally, the accessory (100) can also be configured to receive power from other external sources such as a power adapter connected to a wall outlet, a solar power source, or an independent battery attachment connected to the accessory (100).

In another embodiment of the present disclosure, the accessory (100) can be configured to communicate with the consumer electronic device (102) through the USB port (168), serial port, or a wireless connection such as BLUETOOTH®. Thus, by establishing such a communication link between the accessory (100) and the consumer electronic device (102), the consumer electronic device (102) can be configured to control the turning on and/or off of the heater (158) instead of control being performed by the microcontroller (104) in the accessory (100) as described in the previous paragraphs.

Figure 2:
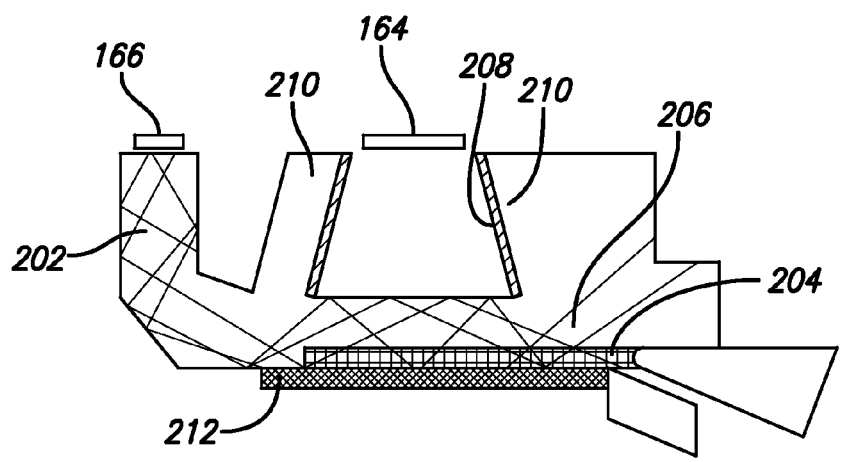
FIGS. 2 and 3A-3B show cross-sectional views of alternative types of the illumination chambers.

In yet a further embodiment, in addition to the light guide (156) on the accessory (100) of FIG. 1, FIG. 2 shows in addition to the light guide (202) of the illumination chamber (206), reflective optics and lenses to further guide the excitation light to the illumination chamber (206) and the reservoir (204). In another embodiment of the present disclosure, a magnifying element such as a lens shaped element in a top portion of the polymer of the illumination chamber (206) can be used to magnify the sample while the emission light are captured by the detector of the consumer electronic device (102) in FIG. 1.

In yet another embodiment as shown in FIG. 2, in order to avoid ambient light from interfering with the light detected by the detector (164) of FIG. 1, a light guiding structure (210) can be established over the reservoir (204) to ensure only the emission light is detected by the detector (164). Furthermore, the interior portions (208) of the light guiding structure (210) can comprise of reflective material to further allow the detector (164) to capture the emission light. The bottom of the illumination chamber (206) can also comprise a metal or polymer layer (212) with reflective properties.

Figure 3A:
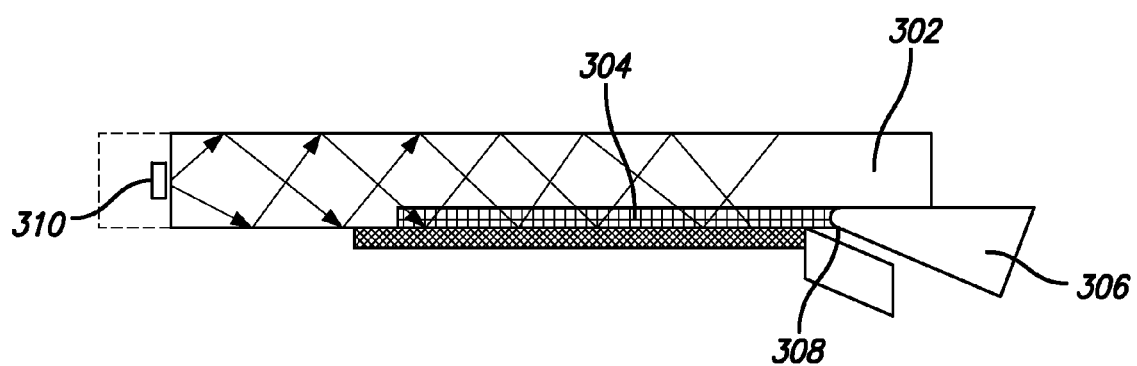
Figure 3B:
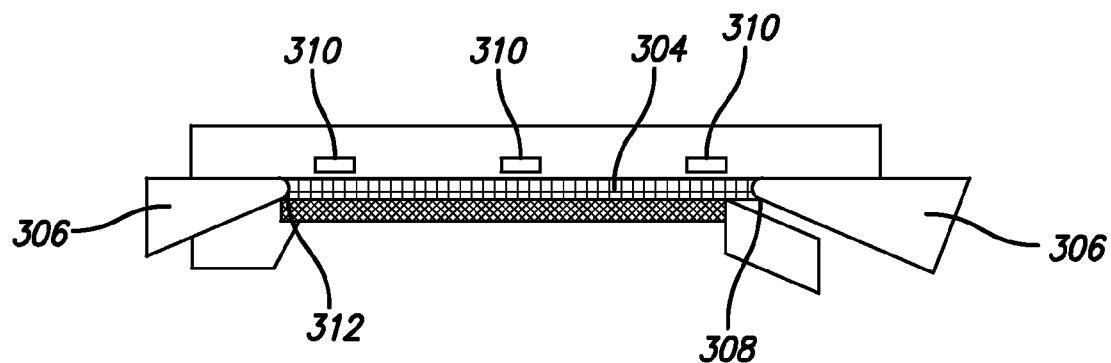

In yet another embodiment as shown in FIGS. 3A-3B, the reservoir (304) in the illumination chamber (302) can be configured to enable depositing of the biological or chemical sample from a side region (308) of the illumination chamber (302) such that even with the accessory (100) and/or the consumer electronic device (102) of FIG. 1 already positioned over the illumination chamber (302), the sample can be easily deposited into the reservoir (304) using a pipette, without disturbing the arrangement. A stopper (306) such as a stop cock can be used to plug the side accessible reservoir (304) of FIGS. 3A-3B to contain and seal the sample to prevent it from spilling, leaking or evaporating. Also shown in FIG. 3B, the reservoir (304) can further comprise a second opening (312) on the side to allow air from the reservoir (304) to escape as the air is displaced by the sample.

In another embodiment, if further cooling of the illumination chamber (150) of FIG. 1 is desired, such cooling procedure can be accelerated by a contact cooling method as described in U.S. patent application Ser. No. 12/638,829. Since contact based cooling takes place in a very short period of time and uses low power, power required for such processes can be supplied by the consumer electronic device (102) as it does not draw large electrical load. Thus, simple and qPCR can be performed compactly and at low cost, thereby enabling the possibility to perform such procedures on-the-field.

In the various configurations of the illumination chambers described herein, the reservoir can be pre-filled with dry reagents, lyophilized reagents, and reagents in paraffin or in liquid form, thereby minimizing the number of steps to be performed while preparing the chemical or biological sample. Thus, only the sample needs to be introduced at the Point of Care (POC) (e.g., on-the-field), further simplifying the sample measurement and/or analysis process. qPCR reagents can also be used to pre-fill the reservoir for cases when a volume fraction of blood is sufficiently large. In cases when the samples are less complex, such as saliva samples and water samples for testing water quality, low cost reagents and enzymes can be used. If desired, the samples can be pre-processed with the reagents by using existing off-the-shelf portable kits.

Figure 5:
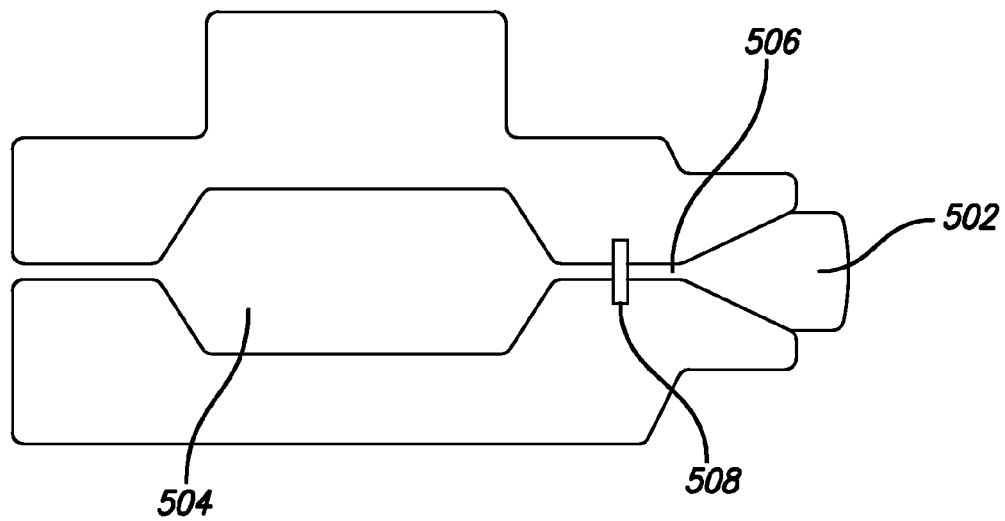

In yet another embodiment as shown in FIG. 5, an open sample area (502) can be provided, which allows the user to deposit the biological or chemical sample, such that the sample enters the reservoir (504) by way of gravity and/or surface tension. A channel (506) connecting the open sample (502) area to the reservoir (504) can be shut by a slit valve (508) to prevent the sample from flowing out of the reservoir (504). If bubbles exist in the sample, the bubbles can be forced out of the top of the reservoir by either slightly tapping the illumination chamber or by vibrating the illumination chamber, depending on the size and characteristics of illumination chamber according to the methods described in the following paragraphs.

Figure 6:
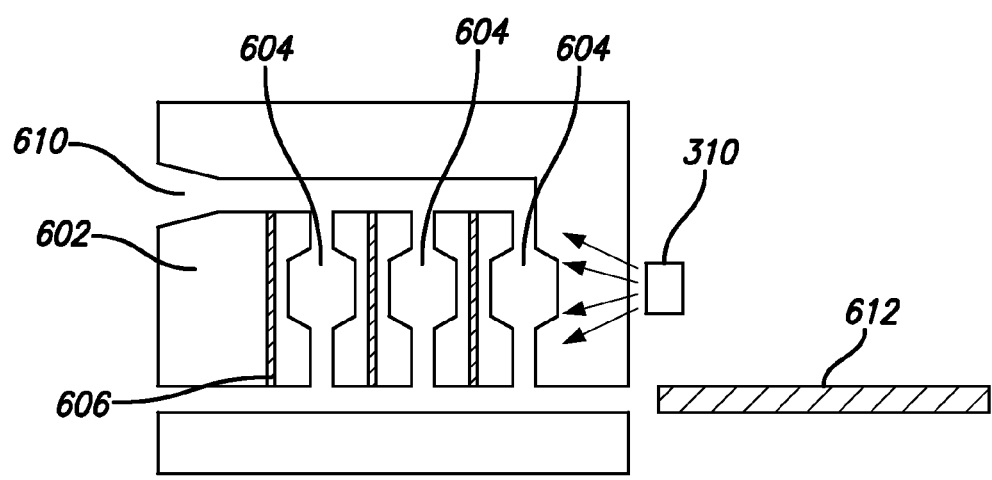

In yet another embodiment as shown in FIG. 6, the illumination chamber (602) can comprise a plurality of reservoirs (604) (multi-well) so that multiple samples can be deposited within a single illumination chamber (602). Such multi-well illumination chamber can be configured such that the sample fluid fills the plurality of reservoirs (604) thought sample inlet (610) by way of gravity, surface adhesion, or surface tension. Regions outside of the reservoirs (604) but within the illumination chamber (612) can be made of hydrophobic material to repel the sample fluid, whereas regions inside of the reservoirs (604) can be made of hydrophilic material to attract the sample fluid, thus further encouraging the sample fluid to enter the reservoirs (604). If there are any bubbles, the bubbles can be forced out according to the methods described in the previous paragraphs. Opposite the sample inlet (610) to the reservoir is a second opening (608) which can allow such bubble or air to escape when filling the reservoirs (604). The sample inlet (610) and the second opening (608) can be sealed with a sliding plug (612), acting like a valve, to completely seal the reservoirs (604).

A single light detector can be used for detecting the emission light from the plurality of reservoirs (604) by establishing optical separators (606) between each of the reservoirs (604) to maintain separation between the emission light emitted from each of the reservoirs (604).

In another embodiment of the present disclosure, as shown in FIGS. 3A, 3B, 4 and 6, the illumination chamber can comprise its own light source (310), such that the light source (e.g., LED) can be embedded within or on the illumination chamber. Furthermore, there can be a plurality of light sources where each of the light sources can be of different colors (e.g., red LED, green LED, white LED). The accessory can further comprise a color filter, positioned in parallel to the excitation filter, to change the color of the excitation light. Similarly, a moveable color filter can be positioned in front of the light detector to allow filtering at different wavelengths for different fluorophores in the sample. In the case where there is a plurality of reservoirs (604) as in FIG. 6, a plurality of light sources (e.g., LEDs) or filters can be used, thus allowing for multiplexing capability.

In a further embodiment of the present disclosure, a similar method can be used, for example, in Enzyme-Linked Immunosorbent Assay (ELISA) procedures. During an ELISA procedure when the biological or chemical sample is desired to be mixed (e.g., mixing and antigen bonding) in the reservoir, the illumination chamber can be placed on a consumer electronic device comprising a vibrating feature (e.g., cell phone), such that when the vibrator of the cell phone is turned on, mixing and bonding of the antigen can take place. The software application on the microcontroller in the accessory or on the consumer electronic device can be programmed such that a user can set a timer for the vibrator so that the vibrator will turn off after a desired amount of time.

Similarly to the embodiments described above in the qPCR system, an accessory can be configured to hold the illumination chamber used in the ELISA procedure on the consumer electronic device to ensure the illumination chamber does not fall of the consumer electronic device while being vibrated.

Mixing procedures similar to the ELISA procedure can be useful in food and water testing while travelling or in remote locations where laboratories are not easily accessible. For example, a plurality of such accessories can be carried by a mobile health team to enable food and water testing when in-the-field.

In a further embodiment, the software application on the consumer electronic device can be programmed to comprise a plurality of features which can allow an untrained person to still operate the measurement and/or analysis system. Some of the features include, by way of example and not of limitation:

Display test results and parameters for the test.

Display temperature and fluorescence graphs for qPCR.

Suggest tests based on patient's symptoms. The application can be interactive, query based or step-by-step guidance.

Display and explain each step to be performed by the user with video and pictures.

Provide contact information and a means for communicating with another person (e.g., administrator, doctor, and subject matter expert) located elsewhere incase help or further advice is needed or desired.

Maintain a log of all tests conducted and results thus obtained.

Maintain patient's credentials (e.g., picture of patient, identification, fingerprint, DNA information, retina scan).

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. An accessory configured to connect a consumer electronic device with an illumination chamber, the consumer electronic device comprising a light source and a light detector, the illumination chamber being provided with a light coupling structure and one or more reservoirs containing biological or chemical samples adapted to produce an emission light, the accessory comprising:
   an excitation filter configured to filter light directed from the light source of the consumer electronic device towards the illumination chamber;
   an emission filter; and
   a light guide, configured to guide the light filtered by the excitation filter towards the illumination chamber,
   wherein:
      the accessory is configured in such a way that when the light detector is aligned over the reservoir, the light source is aligned to be able to provide light through the light guide to the light coupling structure;
      the light coupling structure is configured to couple the excitation light into the illumination chamber to illuminate a sample volume within the reservoir;
      the accessory is configured to guide the excitation light to the illumination chamber and the reservoir via the light guide, the light coupling structure and/or internal reflective surfaces;
      the accessory is configured to filter light emitted by the sample through the emission filter and to direct the filtered light to be detected by the light detector of the consumer electronic device; and
      the excitation filter and the emission filter are aligned between each other so that, when the excitation filter is aligned to the light source of the consumer electronic device, the emission filter is aligned to the light detector of the consumer electronic device.

2. The accessory according to claim 1, further comprising:
   a temperature sensor as part of the accessory, connectable to a heatable element of the illumination chamber;
   a microcontroller as part of the accessory, configured to receive temperature information of the heating element through the temperature sensor and to control the heating element when the illumination chamber is connected with the consumer electronic device through the accessory; and
   an electronic switch as part of the accessory, connected with the microcontroller and configured to turn on or off the heating element according to instructions from the microcontroller.

3. The accessory according to claim 1, wherein the light emitted by the sample is a fluorescence light.

4. The accessory according to claim 2, wherein the microcontroller and the heating element are adapted to receive power from the consumer electronic device through an input/output port.

5. The accessory according to claim 2, wherein the microcontroller and the heating element are adapted to receive power from an external power source through an input/output port.

6. The accessory of claim 4, wherein the input/output port is selected from the group consisting of: a USB port and a serial port.

7. The accessory of claim 5, wherein the external power source is selected from the group consisting of: a battery and a power adapter connected to a wall outlet.

8. The accessory of claim 2, wherein the microcontroller is programmed to instruct the electronic switch to turn on and/or off.

9. The accessory of claim 1, wherein the accessory further comprises a wireless element adapted to communicate with a wireless means for communication of the consumer electronic device.

10. The accessory of claim 9, wherein the wireless element is a BLUETOOTH® connection.

11. The accessory of claim 2, wherein the electronic switch is a transistor.

12. The accessory of claim 1, further comprising, as part of the accessory, at least one color filter configured to change color of light from the light source.

13. The accessory of claim 1, further comprising, as part of the accessory, a light structure adapted to exclude ambient light from interfering with the emission light being detected by the detector.

14. An accessory configured to connect a consumer electronic device with an illumination chamber, the consumer electronic device comprising a light source and a light detector, the illumination chamber being provided with a light coupling structure and one or more reservoirs containing biological or chemical samples to be detected, the accessory comprising:
an excitation filter configured to filter light directed from the light source of the consumer electronic device towards the illumination chamber;
a light guide, configured to guide the light filtered by the excitation filter towards the illumination chamber; and
an emission filter configured to filter, in use, emission light emitted by the illumination chamber, the emission light adapted to be detected by the light detector of the consumer electronic device upon filter through the emission filter;
wherein
the accessory is configured in such a way that when the light detector is aligned over the reservoir, the light source is aligned to be able to provide light through the light guide to the light coupling structure;
the light coupling structure being configured to couple the excitation light into the illumination chamber to illuminate a sample volume within the reservoir such that the excitation light can reflect within the illumination chamber and remain confined within the illumination chamber by way of total internal reflection;
the accessory being configured via the light guide, the light coupling structure and/or internal reflective surfaces to guide the excitation light to the illumination chamber and the reservoir; and
the excitation filter and the emission filter are aligned between each other so that, when the excitation filter is aligned to the light source of the consumer electronic device, the emission filter is aligned to the light detector of the consumer electronic device.

15. A method of connecting a consumer electronic device with an illumination chamber to measure and/or analyze a biological or chemical sample, the method comprising:
providing the accessory according to claim 1;
providing an illumination chamber with one or more reservoirs;
providing a consumer electronic device, the accessory configured to connect the consumer electronic device with the illumination chamber;
aligning the light source of the consumer electronic device to the light coupling structure of the illumination chamber with the light guide on the accessory;
aligning the detector of the consumer electronic device to the illumination chamber, the detector configured to detect the emission light from the illumination chamber; and
measuring and/or analyzing the emission light detected from the biological or chemical sample.

16. The method of claim 15, further comprising establishing a communication link between the consumer electronic device and the illumination chamber through the input/output port.

17. The method of claim 15, further comprising establishing a communication link between the consumer electronic device and the illumination chamber over a wireless connection.

18. The method of claim 15, further comprising connecting a power source to the accessory.

19. The method of claim 18, wherein the power source is selected from the group consisting of: a battery and a power adapter connected to a wall outlet.

20. The method of claim 15, further comprising providing a software application in the consumer electronic device, wherein the software application analyzes the information obtained by the detector.

21. The method of claim 20, wherein the software application is configured to determine a viral load determination of the biological or chemical sample.

22. The method of claim 15, wherein the measuring and/or analyzing is selected from the group consisting of: PCR analysis, qPCR analysis, emission measurement, absorbance measurement, and electrical impedance and voltammetry test.

23. An optical system comprising:
an illumination chamber;
the accessory according to claim 1, the accessory placed on the illumination chamber; and
a consumer electronic device, placed on the accessory.

24. The system of claim 23, wherein the biological or chemical sample is deposited into the reservoir through a side opening in the illumination chamber.

25. The system of claim 24, wherein the side opening is configured to be plugged with a plug.

26. The system of claim 24, wherein the side opening is configured to be plugged with a slit valve.

27. The system of claim 23, wherein the illumination chamber comprises an array of two or more reservoirs, each reservoir being separated with optical separators such that the emission light from each reservoir is segregated.

28. The system of claim 23, wherein the consumer electronic device is selected from the group consisting of: cell phone, smartphone, digital camera, internet tablet, laptop computer, netbook computer, and webcam.

* * * * *